United States Patent
Godara et al.

(10) Patent No.: US 8,343,146 B2
(45) Date of Patent: Jan. 1, 2013

(54) METHODS FOR CONTROL OF ENERGY DELIVERY TO MULTIPLE ENERGY DELIVERY DEVICES

(75) Inventors: Neil Godara, Milton (CA); Taylor Hillier, Mississauga (CA); Matthew Parker, Deep River (CA); Jason Woo, Vaughan (CA)

(73) Assignee: Kimberly-Clark Inc., Ontario (CA)

( * ) Notice: Subject to any disclaimer, the term of this patent is extended or adjusted under 35 U.S.C. 154(b) by 560 days.

(21) Appl. No.: 12/528,193

(22) PCT Filed: Feb. 25, 2008

(86) PCT No.: PCT/CA2008/000367
§ 371 (c)(1),
(2), (4) Date: Sep. 24, 2009

(87) PCT Pub. No.: WO2008/101356
PCT Pub. Date: Aug. 28, 2008

(65) Prior Publication Data
US 2010/0324548 A1 Dec. 23, 2010

Related U.S. Application Data

(60) Provisional application No. 60/891,521, filed on Feb. 25, 2007, provisional application No. 60/891,522, filed on Feb. 25, 2007, provisional application No. 60/891,524, filed on Feb. 25, 2007, provisional application No. 60/891,525, filed on Feb. 25, 2007.

(51) Int. Cl.
*A61B 18/10* (2006.01)

(52) U.S. Cl. .......................................... 606/34; 606/41

(58) Field of Classification Search .............. 606/32–35, 606/41, 45–50
See application file for complete search history.

(56) References Cited

U.S. PATENT DOCUMENTS

| | | | |
|---|---|---|---|
| 4,244,371 A | 1/1981 | Farin | |
| 5,334,193 A | 8/1994 | Nardella | |
| 5,462,521 A | 10/1995 | Brucker et al. | |
| 5,688,267 A | 11/1997 | Panescu et al. | |
| 5,788,688 A | 8/1998 | Bauer et al. | |
| 5,800,432 A | 9/1998 | Swanson | |
| 6,017,338 A | 1/2000 | Brucker et al. | |
| 6,053,912 A | 4/2000 | Panescu et al. | |
| 6,165,169 A * | 12/2000 | Panescu et al. | 606/1 |
| 6,235,022 B1 | 5/2001 | Hallock et al. | |
| 6,273,886 B1 | 8/2001 | Edwards et al. | |
| 6,500,175 B1 | 12/2002 | Gough et al. | |
| 6,506,189 B1 | 1/2003 | Rittman, III et al. | |
| 6,575,969 B1 | 6/2003 | Rittman, III et al. | |
| 6,623,423 B2 * | 9/2003 | Sakurai et al. | 600/104 |
| 6,679,875 B2 * | 1/2004 | Honda et al. | 606/1 |

(Continued)

FOREIGN PATENT DOCUMENTS

DE 43 39 049 5/1995
(Continued)

*Primary Examiner* — Michael Peffley
(74) *Attorney, Agent, or Firm* — Dority & Manning, P.A.

(57) ABSTRACT

Embodiments of a system and method are described for delivering energy to a body of a human or animal through a plurality of energy delivery devices. In some embodiments, a plurality of energy delivery devices are coupled to a generator and the number of energy delivery devices is automatically detectable. Furthermore, in some embodiments, the amount of energy delivered through the energy delivery devices is controlled, at least in part, by dynamically varying the amount of time that each energy delivery device is delivering energy.

12 Claims, 12 Drawing Sheets

U.S. PATENT DOCUMENTS

| | | |
|---|---|---|
| 6,702,810 B2 | 3/2004 | McClurken et al. |
| 6,783,523 B2 | 8/2004 | Qin et al. |
| 6,830,569 B2 * | 12/2004 | Thompson et al. ............. 606/34 |
| 6,899,538 B2 * | 5/2005 | Matoba ........................ 433/114 |
| 6,936,047 B2 | 8/2005 | Nasab et al. |
| 6,939,346 B2 | 9/2005 | Kannenberg et al. |
| 7,137,980 B2 | 11/2006 | Buysse et al. |
| 7,217,269 B2 * | 5/2007 | El-Galley et al. ............... 606/34 |
| 8,012,150 B2 | 9/2011 | Wham et al. |
| 2004/0054365 A1 | 3/2004 | Goble |
| 2005/0137662 A1 | 6/2005 | Morris et al. |
| 2006/0161148 A1 | 7/2006 | Behnke |

FOREIGN PATENT DOCUMENTS

| | | |
|---|---|---|
| DE | 10 2005 007769 | 8/2006 |
| EP | 1 472 984 | 4/2004 |
| WO | WO 2005/107857 | 11/2005 |

* cited by examiner

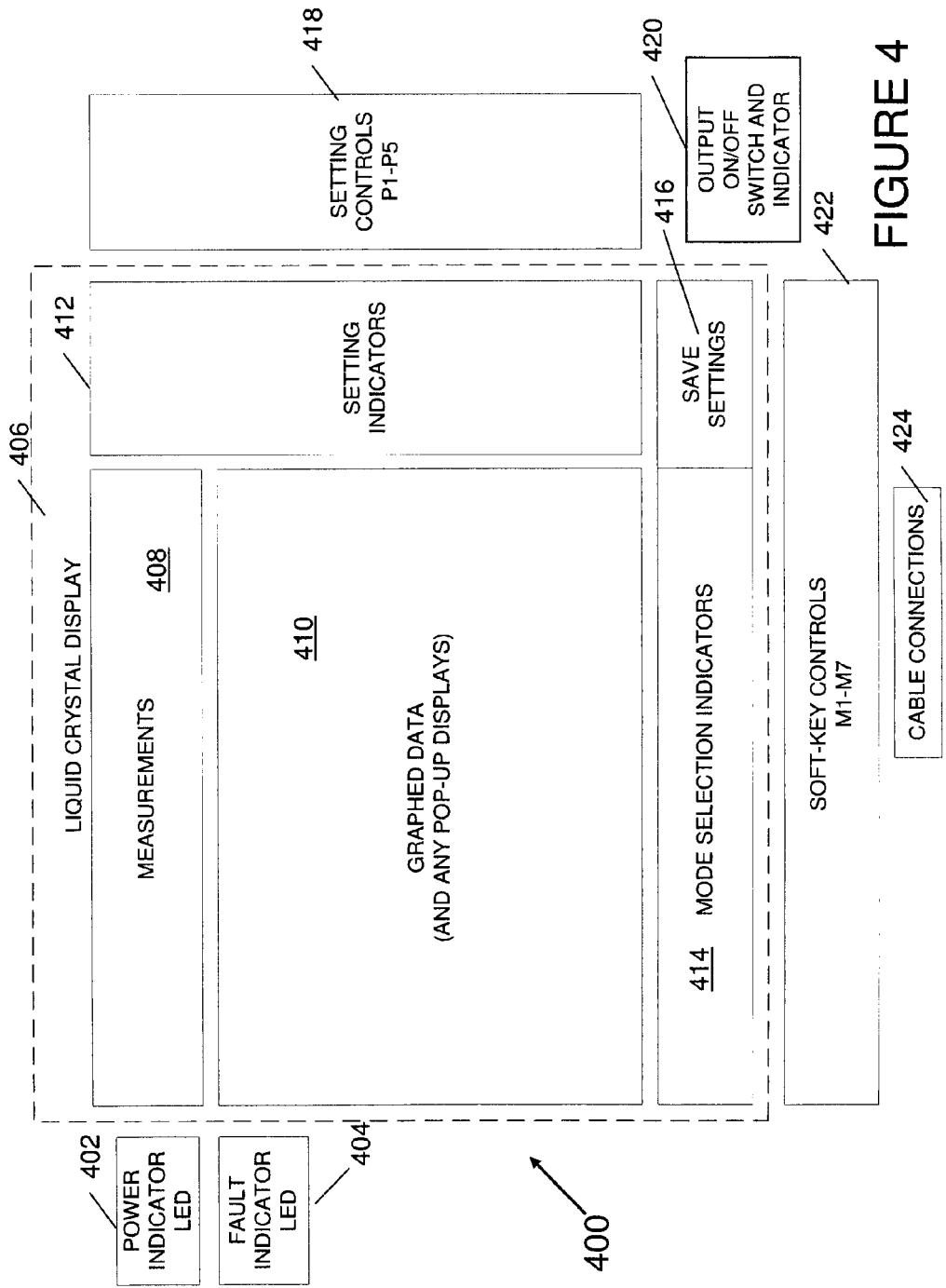

METHODS FOR CONTROL OF ENERGY DELIVERY TO MULTIPLE ENERGY DELIVERY DEVICES

CROSS-REFERENCES TO RELATED APPLICATIONS

This application claims the benefit of U.S. Provisional Patent Application Ser. No. 60/891,521, Ser. No. 60/891,522, Ser. No. 60/891,524 and Ser. No. 60/891,525, all filed on Feb. 25, 2007. All of the aforementioned applications are hereby incorporated by reference in their entirety.

TECHNICAL FIELD

The invention relates to electrosurgical methods. In particular, the inventions relates to methods for controlling energy delivery to a plurality of energy delivery devices.

BRIEF DESCRIPTION OF THE DRAWINGS

In order that the invention may be readily understood, embodiments of the invention are illustrated by way of examples in the accompanying drawings, in which:

FIG. 4 is a schematic view of the components of an embodiment of a front panel user interface for a generator of the present invention;

DETAILED DESCRIPTION

Figure 1:
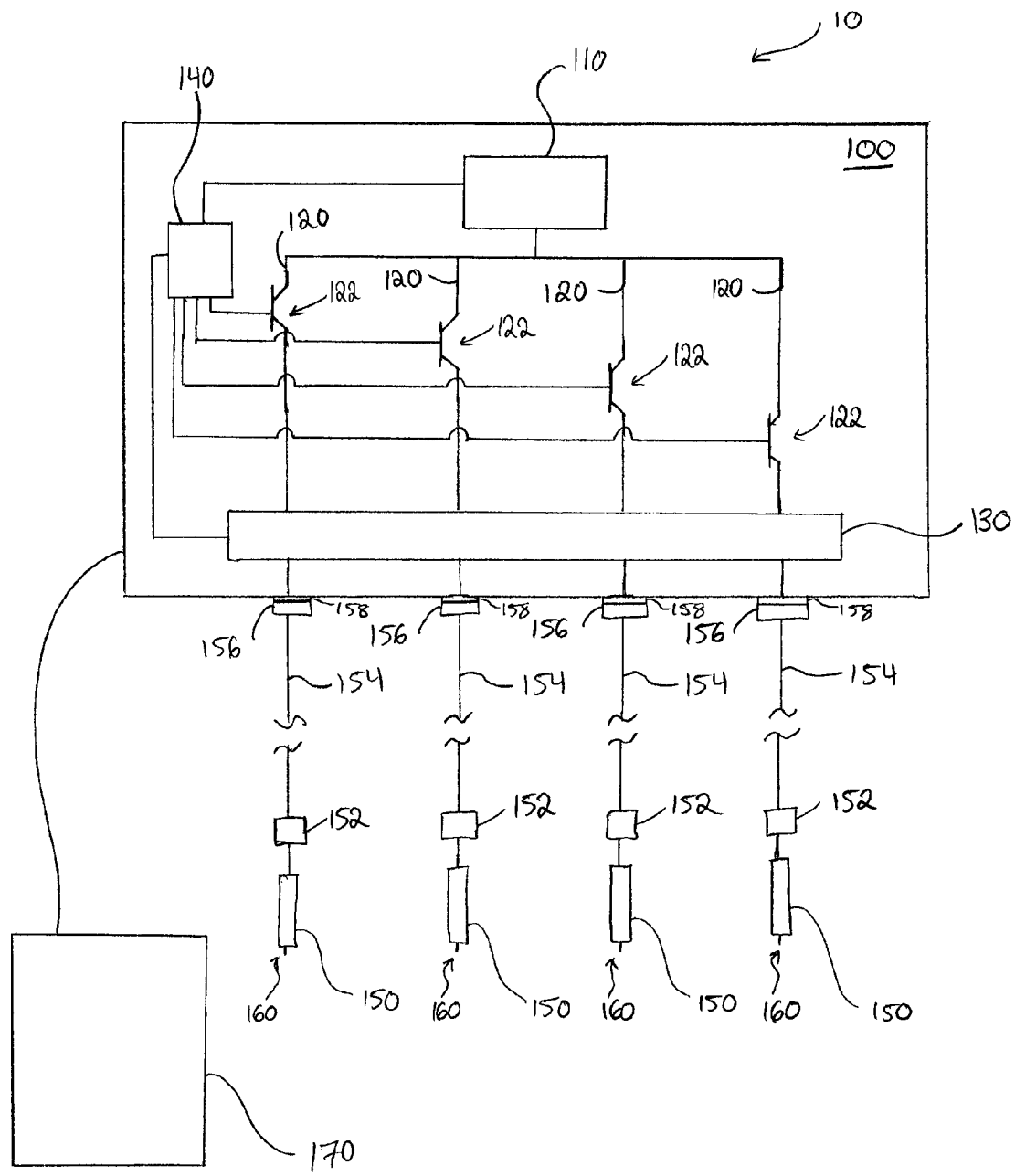
FIG. 1 is a schematic view of an embodiment of a system of the present invention.

In one broad aspect, embodiments of the present invention comprise an electrosurgical system for performing a procedure on a patient's body, the system comprising: a plurality of energy delivery devices, each energy delivery device comprising at least one electrode for delivering electrical energy to a tissue of the patient's body; and an electrical generator for coupling to the plurality of energy delivery devices such that an output of the generator can be delivered via the plurality of energy delivery devices to produce an effect on the tissue of the patient's body, the generator comprising a detector for detecting a quantity of energy delivery devices coupled to the generator.

As a feature of this aspect, the electrical generator is capable of operating in a plurality of functional operating modes, the generator comprising: a mode storage element for storing the operating modes of the generator, the quantity of energy delivery devices being associated with at least one applicable operating mode from the stored operating modes; a mode selector for selecting a current operating mode from the operating modes applicable to the quantity of energy delivery devices detected; and an energy controller for controlling a delivery of energy by said generator in accordance with the current operating mode.

In an additional broad aspect, embodiments of the present invention provide a method comprising: coupling a plurality of energy delivery devices to a generator capable of operating in a plurality of functional operating modes; automatically detecting a quantity of energy delivery devices coupled to the generator; selecting a current operating mode from the plurality of operating modes of the generator responsive to the detected quantity of energy delivery devices; and delivering energy in accordance with the current operating mode.

In a further broad aspect, embodiments of the present invention provide methods for delivering energy to a body of a human or animal through a plurality of electrosurgical probes, whereby the amount of energy delivered through the probes is controlled, at least in part, by dynamically varying the amount of time that each probe is delivering energy.

In some such embodiments, the method comprises: coupling a plurality of probes to a generator; delivering electrical energy from the generator to tissue of the patient's body via the plurality of probes to produce an effect on the patient's body; during the procedure, measuring at least one parameter associated with at least one of the plurality of probes; and controlling an amount of energy delivered by the at least one of the plurality of probes during the procedure, by varying an amount of time that the at least one of the plurality of the probes is delivering energy responsive to the at least one measured parameter.

As a feature of this method aspect, at least one of the plurality of probes is positioned at a first treatment site within the patient's body and at least one other of the plurality of probes is positioned at a second treatment site within the patient's body, the first treatment site and the second treatment site being comprising different tissues.

As a further feature, an electrosurgical system for performing the method is provided, the system comprising: a plurality of electrosurgical probes, each probe comprising at least one electrode for delivering electrical energy to a tissue of the patient's body, at least one of the probes comprising at least one sensor for measuring a parameter indicative of a property of the tissue to which energy is delivered; an electrical generator for coupling to the plurality of probes such that an output of the generator can be delivered to each of the plurality of probes; a measurement interface for receiving at least one parameter measurement from the at least one sensor; and a controller for controlling the output of the generator in accordance with a respective probe duty cycle, the controller being coupled to the electrical generator and to the measurement interface and operable to adjust one or more of the respective probe duty cycles responsive to the at least one parameter measurement.

As a feature of this aspect, each probe comprises at least one sensor for measuring a parameter indicative of a property of the tissue to which energy is delivered by the probe.

In an additional broad aspect, a method for controlling an electrosurgical generator during a treatment procedure is provided, the generator delivering energy in accordance with one or more controllable energy delivery parameters directly controllable by the generator and one or more dependent energy delivery parameters not directly controllable by the generator, the method comprising: measuring at least one tissue parameter indicative of a property of a tissue; and modifying a value of at least one of the controllable energy delivery parameters in response to the at least one measured tissue parameter, in order to modify a value of at least one of the dependent energy delivery parameters.

As a feature of this aspect, an electrosurgical system for performing the method is provided. The system comprises: a plurality of energy delivery devices, each energy delivery device comprising at least one electrode for delivering electrical energy to a tissue of the patient's body, at least one of the energy delivery devices comprising at least one sensor for measuring at least one parameter indicative of a property of the tissue to which energy is delivered; an electrical generator for delivering energy to the tissue via the energy delivery devices; and a controller for controlling an output of the electrical generator in accordance with one or more directly controllable energy delivery parameters and one or more dependent energy delivery parameters not directly controllable, wherein the controller is operable to modify a value of at least one of the controllable energy delivery parameters in order to modify a value of at least one of the dependent energy delivery parameters responsive to at least one of the parameters measured by the at least one sensor.

In another broad aspect, embodiments of the present invention comprise a computer readable medium including computer-executable instructions for interfacing with an electrosurgical generator during a treatment procedure, the computer-executable instructions performing one or more of the aforementioned methods.

As a feature of this aspect, the computer readable medium includes, but is not limited to, a floppy disk, a hard disk, a CD/DVD ROM, a flash memory device, and non-volatile ROM and RAM.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 shows an embodiment of a system 10 in accordance with the present invention comprising: a generator 100, a plurality of energy delivery devices 150 and a dispersive electrode 170. In the illustrated embodiment, generator 100 comprises an energy source 110, one or more output channels 120 and a controller 140 for controlling the delivery of energy by generator 100. Furthermore, in this embodiment, each output channel 120 comprises a switching means 122 operatively coupled to controller 140. In addition, in this embodiment, generator 100 comprises a measurement interface 130 for receiving information from one or more sensors 160 operatively coupled to generator 100, as will be described further herein below.

Energy source 110 may be any source capable of supplying AC electromagnetic energy, for example, an electrosurgical generator. In some embodiments, the energy supplied by energy source 110 has a frequency in the radiofrequency (RF) range (for example, a frequency of between about 400 kHz and about 900 kHz), a voltage output of between about 0 V and 160 V and a maximum power output of about 50 W at a current output of about 0.9 A.

In the embodiment of FIG. 1, a plurality of output channels 120 are connected to energy source 110. Output channels 120 are connected in parallel to energy source 110, such that only one energy source 110 is required to supply energy to all output channels 120. Output channels 120 are independently controllable, in that they may each be independently controlled by controller 140 via switching means 122.

Switching means 122 comprises any component that may be controllable at high frequencies (for example, in the RF range) to at least substantially permit the flow of current through a channel 120 or substantially prevent the flow of current through a channel 120. In some embodiments, switching means 122 is further operable to limit the flow of current without substantially preventing it entirely. For example, in one embodiment, switching means 122 comprises a transistor, for example a field-effect transistor (FET) that is operatively coupled to controller 140 such that the application of an electronic signal from controller 140 to the transistor results in the transistor acting effectively as a high frequency electronic switch, either substantially permitting the flow of current (in a 'closed' state) or preventing the flow of current (in an 'open' state).

Controller 140 comprises, in some embodiments, one or more of a processor, a memory and any other functional components necessary to interface with energy source 110, switching means 122 and measurement interface 130. Controller 140 may be substantially software-based, hardware-based or a combination of hardware and software. Controller 140 is operable to interface with energy source 110 to control the delivery of energy therefrom, for example in response to parameter measurements received from measurement interface 130. In addition, controller 140 is operable to interface with switching means 122 in order to control the flow of current through one or more of the output channels 120. Furthermore, controller 140 is operable to control generator 100 to deliver energy to each of the plurality of energy delivery devices, for example probes, in accordance with a respective duty cycle, and controller 140 is further operable to adjust one or more of the respective duty cycles in response to the parameter measurements, as will be described further herein below with respect to a method aspect of the present invention.

Energy source 110 is operatively coupled, as will be described further herein below, to one or more, for example a plurality of, energy delivery devices 150, for delivering energy to a body tissue. Energy delivery devices 150 may be any of a variety of energy delivery devices including, for example: probes, as will be described further herein below; other electrodes including plate electrodes; or multiple electrodes on a single probe. In embodiments comprising a plurality of energy delivery devices 150, the energy delivery devices 150 may have different configurations. For example, the length, gauge and/or other properties of the energy delivery devices 150 may differ.

In the context of the present invention, the term 'probe' is used to describe any elongate device that may be inserted in a minimally-invasive manner into a patient's body (with or without the aid of additional devices, such as, but not limited to, needles or introducers, or supporting or stereotactic devices). These devices include, but are not limited to catheters, cannulae, and electrosurgical probes, including probes with multiple electrodes. For the sake of clarity, the term 'probe' is used throughout the specification to specify any such device. Furthermore, it should be understood that in any embodiment of the present invention, two or more electrically connected devices may be used in place of a single 'probe'. In other words, a system comprising a plurality of probes includes more than one elongate device, although any of the elongate devices may include a plurality of electrodes. Having a plurality of elongate devices allows a user to position each such device at a substantially different location within a patient's body, for example to treat two different tissues during a single course of treatment.

In the illustrated embodiment, energy delivery devices 150 are coupled to energy source 110 via distal connectors 152, cables 154, proximal connectors 156, generator connectors 158 and output channels 120. One output channel 120 may connect to a single energy delivery device 150, or may connect to multiple energy delivery devices 150.

Energy source 110 may be configured to deliver energy through one or more energy delivery devices 150 in a monopolar, bipolar, multipolar and/or multiphasic configuration. When energy delivery devices 150 are operated in a monopolar configuration, dispersive electrode 170, for example a grounding pad, is used to provide a path for the electrical current to flow to the circuit ground.

In some embodiments, at least one of energy delivery devices 150 may be associated with a sensor 160, which may comprise, for example, a temperature sensor such as a thermocouple, thermistor, thermometer, or other temperature sensing device. A sensor 160 may be physically connected to an energy delivery device 150, or may be separate (for example, a temperature sensor may be situated on a separately insertable probe or needle), as long as it is capable of sensing a temperature indicative of the temperature of a tissue in which the device with which it is associated is inserted. Sensors 160 may be operatively coupled to measurement interface 130 in order to provide feedback for control of electrical components 130 or any other part of system 200.

Measurement interface 130 is operable to receive signals from sensors 160 and to interface with controller 140. In some embodiments, measurement interface 130 is operable to process the signals received from sensors 160 and to transmit a result of the signal processing to controller 140, in order to enable controller 140 to effectively control the delivery of energy from energy source 110 in response to measurements of a tissue property provided by sensors 160. In alternate embodiments, the processing of the signals received from the sensors is performed external to the generator, for example within proximal connectors 156 or generator connectors 158.

One exemplary embodiment of a system 10 of the present invention comprises an electrosurgical generator 100 and four electrosurgical probes. The four electrosurgical probes are configured to deliver energy in a monopolar configuration through a patient's body to a grounding pad operatively connected to the generator 100 to provide a path to circuit ground. Each probe comprises a thermocouple located at or adjacent to the tip of the probe, each thermocouple being capable of sensing a temperature indicative of a temperature of tissue adjacent the probe with which it is associated. The thermocouples are operatively coupled to measurement interface 130, which is in turn operatively coupled to controller 140, allowing controller 140 to control the delivery of energy from energy source 110 in response to one or more measurements made by a thermocouple. If, for example, a temperature measured by a thermocouple connected to a probe is higher than an expected or pre-set temperature, controller 140 may reduce the current delivered to that probe, for example by reducing the time during which current is delivered to that probe, as will be described further herein below.

Figure 2:
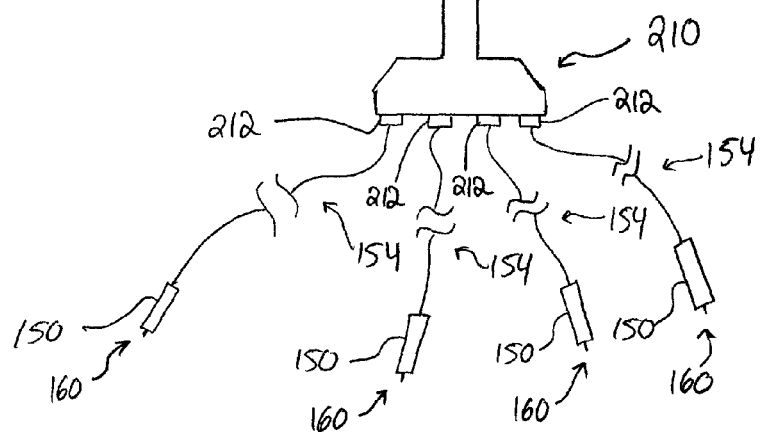
FIG. 2 is a plan view of an embodiment of a cable that may be used in a system of the present invention.

With reference now to FIG. 2, rather than comprising separate cables 154, one for each energy delivery device 150, some embodiments comprise a single cable 204 for operatively coupling a plurality of energy delivery devices 150 to generator 100. In such embodiments, cable 204 may be coupled to generator 100 via generator connector 200 and proximal cable connector 202 and may be coupled to energy delivery devices 150 via a plurality of distal connectors 212 at cable distal hub 210. These embodiments reduce the amount of cabling present in the system and may thereby reduce the clutter present in an operating theatre during a treatment procedure. In addition, such embodiments allow energy delivery devices 150 to be coupled closer to the patient's body, which allows a user to readily determine which energy delivery device is coupled to which connector without having to trace the cabling back to generator 100. Furthermore, in such an embodiment, energy delivery devices 150 do not require (although they may be present, for example as provided below) unique visual identification means, for example color-coding, in order to determine which energy delivery device 150 is connected to which generator connector, because the connections are made at cable distal hub 210, located closer to the patient's body and thus readily discernable to a user. However, in some embodiments, color-coding is provided in conjunction with cable 204, in which case the user may have the ability to assign the color-coding scheme, for example by connecting a particular color to a desired connector 212 at cable distal hub 210.

In some embodiments, generator 100 is capable of automatically detecting the number of energy delivery devices 150 coupled to generator 100, as will be described further herein below. Automatic detection of the number of energy delivery devices 150 coupled to generator 100 obviates the need for a user to manually indicate the number of energy delivery devices 150 coupled to generator 100.

Figure 3:
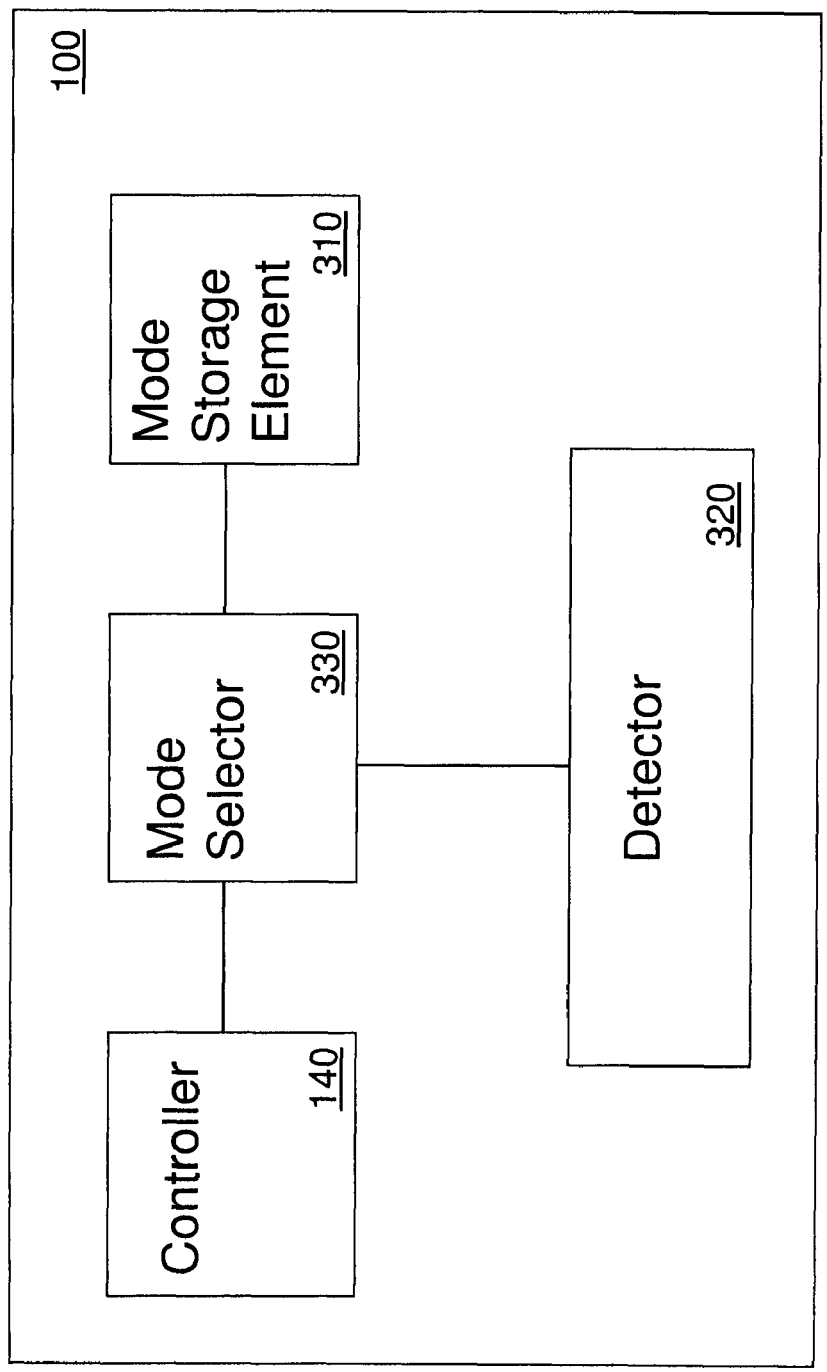
FIG. 3 is a block diagram of an embodiment of a generator of the present invention.

In some such embodiments, generator 100 is capable of operating in a plurality of functional operating modes, including but not limited to: multiple-probe standard RF mode; multiple-probe pulsed RF mode; voltage and/or current stimulation mode; manual standard RF mode; automatic standard RF mode and automatic pulsed RF mode. These and other modes are described in greater detail in co-pending U.S. patent application Ser. No. 10/122,413, filed on Apr. 16, 2002, incorporated herein by reference. In some such embodiments, as shown for example in FIG. 3, generator 100 comprises: a mode storage element 310 for storing the operating modes for the generator; a detector 320 for detecting the number (i.e. quantity) of energy delivery devices 150 operatively coupled to generator 100, where at least one of the stored operating modes is applicable to the number of energy delivery devices 150 detected; a mode selector 330 for selecting a current operating mode from the operating modes applicable to the number of energy delivery devices detected; and an energy controller, for example controller 140, for controlling a delivery of energy by generator 100 in accordance with the current operating mode.

In some such embodiments, the number (i.e. quantity) of energy delivery devices 150 coupled to generator 100 dictate, at least partially, which functional modes are available to the user. Thus, for example, if a plurality of energy delivery devices 150 are coupled to generator 100 and detected by detector 320, certain modes may be made available to the user while, if only one energy delivery device 150 is coupled to generator 100, another mode or modes may be made available. In one exemplary embodiment, a manual power mode, in which a user maintains control over the power output of the generator, is only applicable when a single energy delivery device 150 is connected, while other modes, such as for example multiple-probe standard RF mode, are only applicable when a plurality of energy delivery devices 150 are connected. In some embodiments, the detection of the number of energy delivery devices 150 coupled to generator 100 is performed automatically by the generator. In alternate embodiments, a user may initiate the detection by, for example, pressing a button or other user control.

In addition to the number of energy delivery devices 150 coupled to generator 100, the modes that are applicable to a given system configuration may also depend on the types of energy delivery devices 150 coupled to generator 100. Further details regarding this aspect are described in U.S. patent application Ser. No. 10/122,413, filed on Apr. 16, 2002, previously incorporated herein by reference. For example, certain modes may only be available to energy delivery devices having associated thermocouples and/or thermistors, while certain other modes may only be available to energy delivery devices operable for performing one particular type of procedure.

In certain configurations, where a plurality of operating modes are applicable to the quantity of energy delivery devices 150 (i.e. the number of devices 150) coupled to generator 100 and detected by detector 320, mode selector 330 is operable to select one of the applicable operating modes as the current operating mode. Generator 100 may further comprise user input controls to allow a user to select the current operating mode from the operating modes applicable to the quantity of energy delivery devices 150 coupled to generator 100.

Mode storage element 310 and mode selector 330 may be implemented using software methods exclusively or using a combination of hardware and software. Detector 320, in some embodiments, is implemented using hardware, software or a combination thereof to determine the number of energy delivery devices 150 actually coupled to generator 100. For example, this may be determined by one or more of measuring the impedance of each output channel 120 (wherein a high impedance may be indicative of an open connection, i.e. with no energy delivery device 150 coupled to the output channel 120) and/or sensing a signal from a temperature sensor associated with energy delivery devices 150 using measurement interface 130 (wherein the lack of a sensed signal or a sensed signal outside a pre-determined range may indicate that an energy delivery device 150 is not coupled to generator 100). For example, in one such embodiment, any output channel 120 having a temperature reading between about 15° C. to about 100° C. associated with it is determined to have an energy delivery device connected to it. Alternatively, any output channel 120 that has an associated impedance measurement between about 25 Ohms and about 3000 Ohms is determined to have an energy delivery device connected to it. In further embodiments, other parameters associated with energy delivery devices are used to determine whether or not an energy delivery device is connected to a particular channel.

Alternatively or in addition, each energy delivery device 150 may comprise an identifier that may be detected when energy delivery device 150 is plugged into distal connectors 152 or 212. For example, the identifier may comprise an electrical component, for example a resistor, mounted onto a connector, for example between particular pins of the connector, associated with an energy delivery device 150 or a cable 154. In such an embodiment, if no energy delivery device 150 is connected to a particular connector 152 or 212, then that connector would appear as a short circuit to detector 320. However, any connectors 152 or 212 to which an energy delivery device 150 is in fact connected would appear to the detector 320 as a set of parallel resistors whose total value may be used to determine the number of energy delivery devices connected. For example, in one such embodiment, each energy delivery device 150 or cable 154 has an associated impedance (comprising a resistor soldered across two pins of an associated electrical connector) of about 10 kOhms. I such an embodiment, if two such energy delivery devices are coupled to the system, then detector 320 would detect an overall impedance of about 5 kOhms. Similarly, if 3 energy devices were to be connected, the total impedance would be about 3.3 kOhms and, for 4 energy delivery devices, it would be about 2.5 kOhms. Further details regarding such identifiers may be found in U.S. patent application Ser. No. 10/122,413, filed on Apr. 16, 2002, previously incorporated herein by reference. For example, U.S. patent application Ser. No. 10/122,413 includes the following information:

"The connector cable contains the technology that allows the Probe Type Detector to identify the probe. Specifically, on the end of each connector cable that connects to the cable connection, there is a medical 14 pin connector. In all compatible cables, pins 1, 2, 3 of the 14 pin connector are the identity pins. These identity pins can be shorted together or have a resistance attached across them in order to allow the generator to identify what probe is going to be attached.

The Probe Type Detector circuitry consists of resistors connected in series. This connection creates a voltage divider that is modified by reading the voltage coming from the three identification pins. This voltage is changed by creating electrical shorts between pins or by connecting resistors across them. The resulting voltage is converted to an ADC count through an analog to digital converter and each probe type is assigned its own ADC count."

In some embodiments, generator 100 does not comprise a detector 320. In such embodiments, a user may manually input the number of energy delivery devices connected to generator 100 and mode selector 330 may be operable to select one of the operating modes applicable to the number of probes coupled to the generator as the current operating mode.

In accordance with some embodiments of the present invention, generator 100 comprises a front panel user interface 400 (illustrated schematically in FIG. 4), which can be described as follows. A power indicator LED 402 indicates if the power if turned on. A fault indicator LED 404 indicates if a fault has been detected. The liquid crystal display 406 comprises five general areas. The measurement area 408 is where values measured are displayed. A graphed data and pop up display area 410, a setting indicators area 412, a mode selection indicators area 414 and a save settings area 416 are provided. Hardware setting controls P1 to P5 418 are provided. An output on/off indicator 420, a series of soft key controls M1 to M7 422 and cable connection outlets 424 are also provided on the front panel user interface. The setting controls P1 to P5 418 are inputs to the setting indicators 412. The soft key controls M1 M7 422 are inputs to the mode selection indicators 414.

Figure 5A:
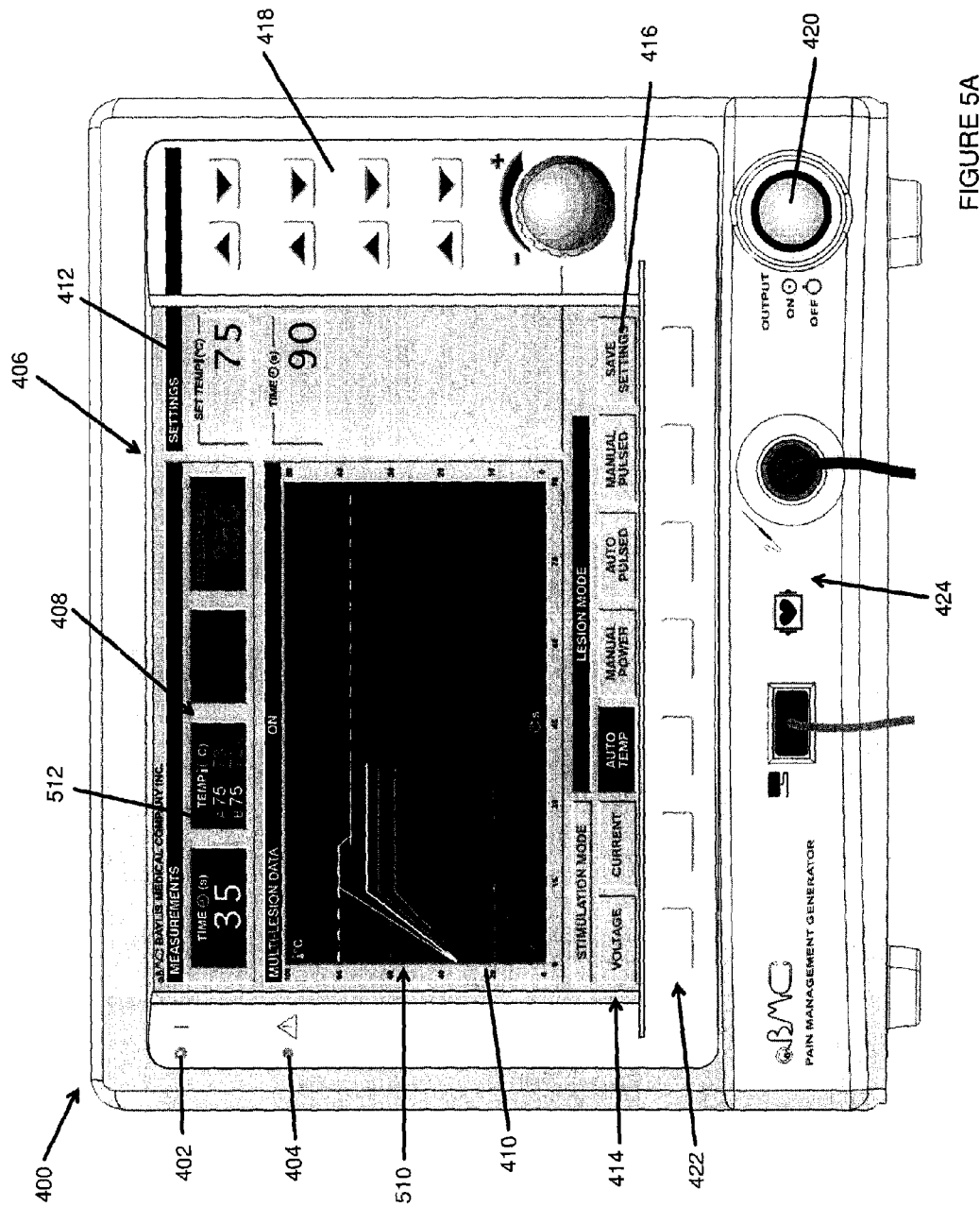
FIGS. 5A and 5B are front elevation views of an exemplary embodiment of the front panel user interface of FIG. 4.
Figure 5B:
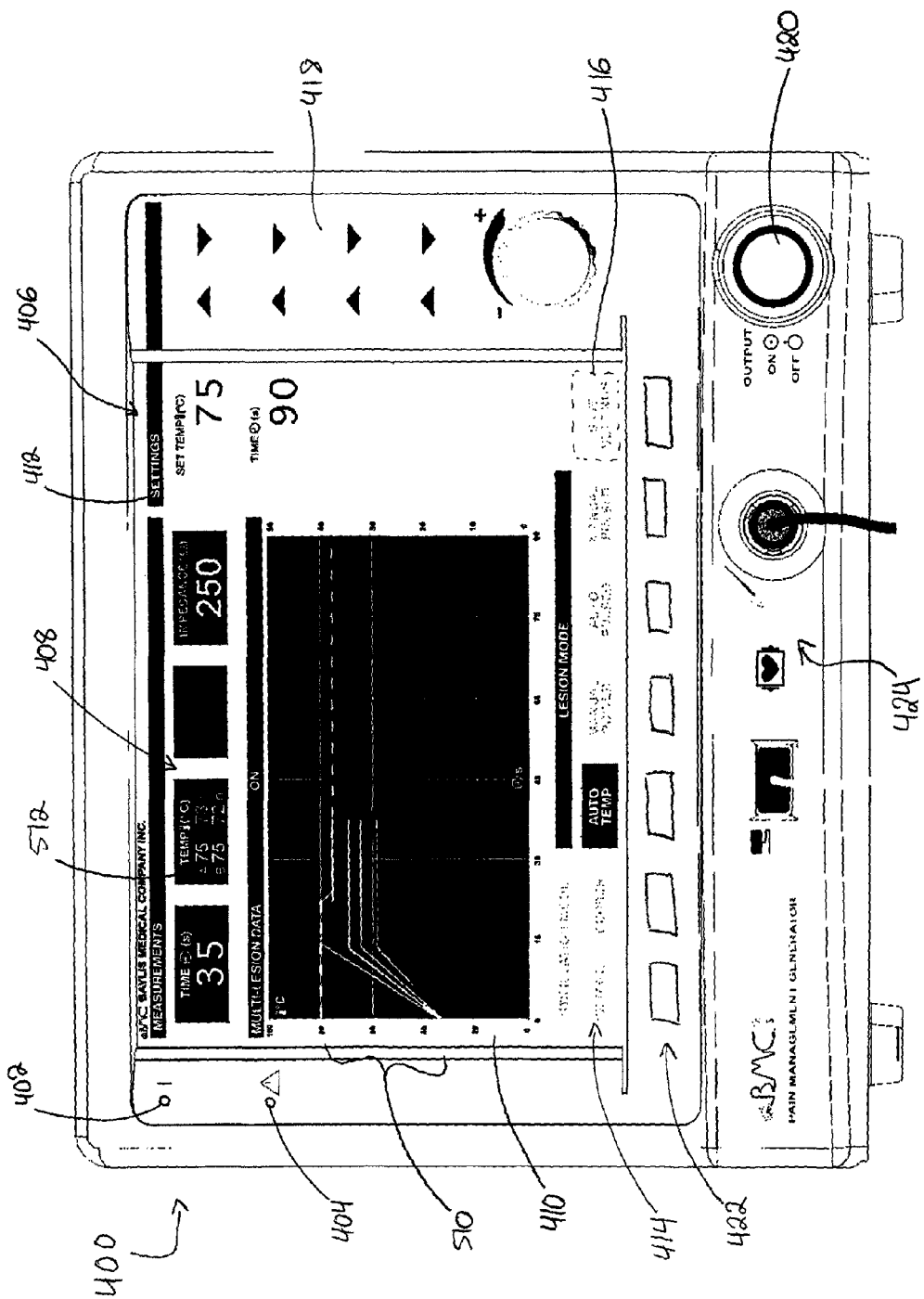

With reference now to FIGS. 5A and 5B, an exemplary embodiment of a front panel user interface 400 is shown. In this embodiment, display area 410 is operable to display at least one plot, for example a substantially real-time, continuous plot, graphing one or more parameters over time. For example, as illustrated in FIGS. 5A and 5B, one or more temperature plots 510 may be displayed simultaneously on display area 410. Advantageously, embodiments of the present invention are operable to display multiple temperature plots 510 substantially simultaneously and substantially in real-time, all on a single graph. Each of the temperature plots 510 may, for example, be indicative of a temperature associated with a particular energy delivery device 150. Displaying multiple plots on a single graph allows a user to more readily compare the different plots than if they would each be displayed on a separate graph. In addition, having a single graphing window allows for more efficient utilization of the space available on display area 410. In some embodiments, the number of temperature plots 510 displayed on display area 410 is determined by the number of energy delivery devices 150 detected by detector 320. Thus, for example, if a single energy delivery device 150 is detected, only one temperature plot is displayed, whereas if four energy delivery devices 150 are detected, four plots are displayed.

In addition to displaying multiple plots on display area 410, embodiments of the present invention are further operable to display a plurality of discrete parameter measurements, for example discrete temperature measurements 512, within measurement area 408. As described with respect to the multiple plots, displaying multiple temperature measurements 512, each corresponding, for example, to a discrete temperature value associated with a particular energy delivery device 150, within a single window within measurement area 408, allows a user to more readily compare the different values than if they would each be displayed within separate windows. Furthermore, in some embodiments, as described herein above, the number of discrete temperature measurements 512 displayed within measurement area 408 is determined by the number of energy delivery devices 150 detected by detector 320. Thus, for example, if a single energy delivery device 150 is detected, only one temperature measurement is displayed, whereas if four energy delivery devices 150 are detected, four measurements are displayed. In some embodiments, symbols such as dashes, for example, are displayed within the window for any energy delivery device 150 for which no temperature measurement is displayed.

Figure 6:
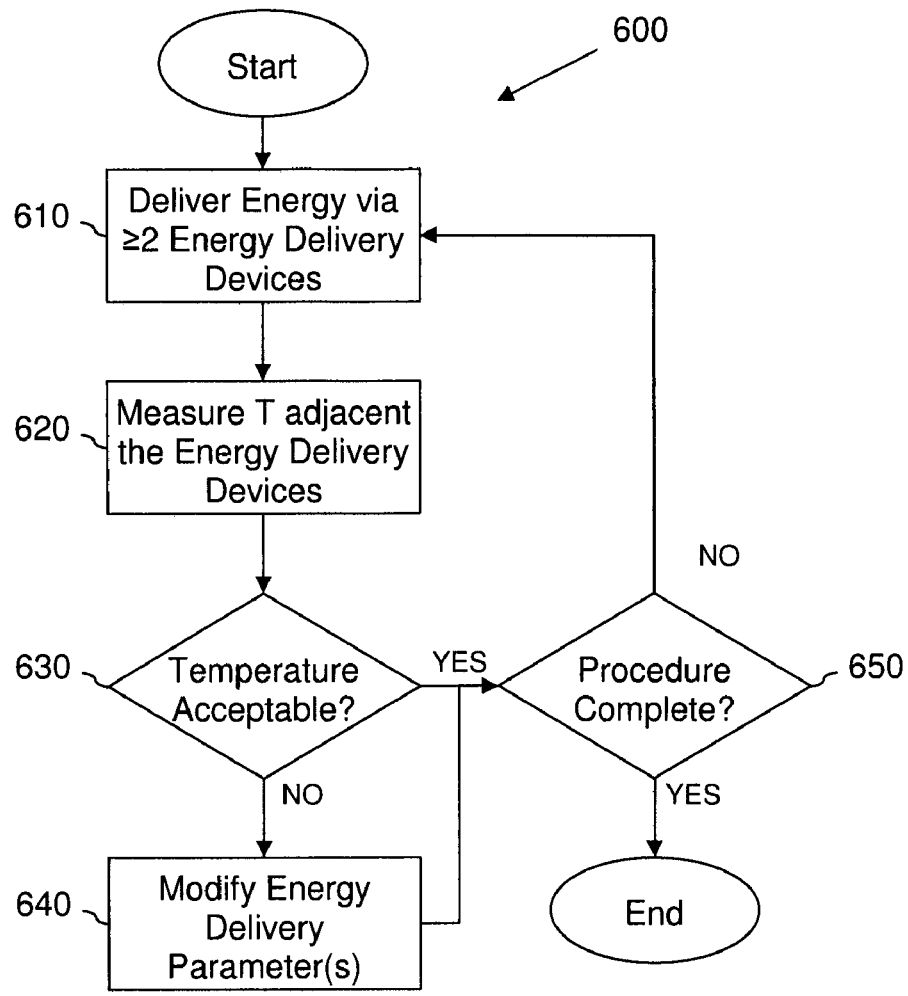
FIG. 6 is a flow chart showing a general embodiment of a method of delivering energy to a body of a human or animal using a plurality of energy delivery devices.

In accordance with another aspect of the invention, embodiments of a method are provided for treating a patient using an embodiment of a system of the present invention. One general embodiment of the method 600 of the present invention is depicted in FIG. 6 as comprising the following steps: at step 610 energy is delivered to a patient from an energy source through at least two energy delivery devices; at step 620, a parameter is measured which is indicative of a temperature in the vicinity of said energy delivery devices 620; at step 630, the measured parameter is assessed, and, if the assessment determines that a parameter is unacceptable, the method proceeds to step 640, whereby at least one energy delivery parameter is modified.

The generator or system described herein above may be used in association with embodiments of the method of the present invention, but in general, the method may be accomplished with any suitable system comprising an energy source operatively coupled in parallel to a plurality of energy delivery devices.

At step 610, delivering energy may involve delivering energy through the at least two energy delivery devices in any of a variety of configurations, for example, in a monopolar configuration, whereby energy may be delivered via one or more energy delivery devices through a patient's body to a separate return electrode, or in a bipolar configuration, whereby energy flows substantially between two or more energy delivery devices. If two or more energy delivery devices are used in a bipolar configuration, any device may be an active or return electrode. In further embodiments, energy delivery devices may be configured in a multipolar or multiphasic arrangement, whereby the energy delivery devices are configured such that the electrical potential and/or the phase of energy transmitted to at least two of the energy delivery devices differs in such a way to cause energy to flow in a desired direction between the energy delivery devices. The energy delivered may be high-frequency electromagnetic energy (such as radiofrequency (RF) energy).

The delivery of energy may be delivered substantially sequentially, substantially concurrently, or partially concurrently, as will be described further herein below. For example, in order to deliver energy to a plurality of energy delivery devices substantially concurrently, the controller may be operable to effectively 'close' the switching means associated with the output channels to which the energy delivery devices are coupled, thus substantially allowing current to flow through a plurality of output channels substantially concurrently.

Depending on the voltage provided to the patient, the energy may generate sufficient heat in the tissue to cause lesions due to ablation or coagulation. In the context of the present invention, 'ablation' refers to raising the temperature of a tissue such that at least a portion of the tissue is coagulated and a lesion is formed within the tissue. In other embodiments, tissue may be vaporized, creating a gap or hole in a tissue.

In an alternate embodiment, the energy delivery may not generate sufficient heat to cause lesions but may rather treat pain by delivering energy in time-separated pulses in order to effectively denervate the tissue. In this context, "time-separated pulses" refers to an energy delivery scheme in which the energy delivered to a particular probe is not continuous, such that, for a particular probe, there is a substantial gap between periods of energy delivery during which no energy is delivered. In such an embodiment, it may be beneficial to deliver the energy to a plurality of energy delivery devices substantially concurrently as described herein above. Alternatively, depending on the desired pulse width and frequency, the energy may be delivered to the plurality of energy delivery devices at least partially sequentially. This may allow for more energy to be delivered to each individual energy delivery device, since the effective impedance load seen by the generator will be increased if the number of probes delivering energy at a given point in time is decreased. For example, if 4 energy delivery devices are used, each with an impedance of about 200 Ohms, then connecting all 4 energy devices to the generator will typically result in a "total impedance" of about 50 Ohms, as seen by the generator. In such an embodiment, applying 50 V to all of the energy delivery devices substantially concurrently will result in a current output of about 1 A, which may be the limit of the generator. In this embodiment, it may rather be desirable to deliver energy to each energy delivery device sequentially, e.g. 20 ms to Probe A, 20 ms to Probe B, 20 ms to probe C, 20 ms to probe D, off for 440 ms . . . 20 ms to Probe A etc., which would result in the delivery of 20 ms pulses at a frequency of 2 Hz. Sequential delivery of energy in this manner may increase the impedance seen by the generator and may therefore increase the available current to the probe that is delivering energy at a given point in time. Sequential delivery of energy also allows for individual feedback-based (e.g. PID loop) temperature control of each individual probe. In alternate embodiments, the delivery of energy to the various probes may be at least partially concurrent, for example in order to prevent transients from being applied (at undesirable frequencies).

The characteristics of the energy being delivered (for example, the voltage, power, current, or frequency) may change throughout a course of a treatment and may vary based on one or more of, but not limited to, user input, characteristics of any element of a system being used an association with the method of the invention, a calculated or measured parameter, or total treatment time elapsed.

Step 620 comprises measuring a parameter indicative of a temperature in the vicinity of the energy delivery devices delivering energy at step 610. This measurement may involve measuring the temperature of the energy delivery device itself, if said temperature is indicative of the temperature of the tissue in which it is placed. In other embodiments, the temperature of the tissue may be inferred by some other means, or may be measured directly, for example, using a probe that extends from the surface of an energy delivery device, or by using a temperature sensor that independently contacts the tissue. Step 620, measurement of a parameter indicative of temperature, need not necessarily occur following step 610, delivering energy. Rather, step 620 may occur substantially concurrently with step 610 and may occur multiple times throughout a treatment procedure. Depending on the particular application, step 620 may be performed for any or all of the energy delivery devices coupled to the generator.

The assessment of one or more measured parameters at step 630 may include, but is not limited to, one or more of: the direct comparison of one or more temperature measurements with one or more expected or pre-determined parameters (for example, accepting any temperature below a preset upper limit of 80° C., or above a preset lower limit of 60° C.); comparing a measured parameter to a previously measured parameter (for example, rejecting any temperature that is >20° C. above the previous measurement for the same device); averaging or otherwise comparing one or more expected parameters (for example, accepting any temperature that is within 5° C. of an average temperature and/or within 25° C. of other measured temperatures); analyzing one or more measured parameters, for example using a PID algorithm; or comparison of a measured parameter to another treatment parameter such as such as total treatment time elapsed, known tissue characteristics, patient history, or characteristics of the energy being delivered. The assessment of one or more measured parameters at step 630 may optionally comprise the generation of one or more calculated parameters (for example, an average temperature value).

If the assessment of the measured parameters at step 630 results in the rejection of one or more of the measurements, one or more parameters of energy delivery are modified at step 640. For example, if a temperature is found to be too low, the following may occur: the energy delivered by the generator to the energy delivery device may be increased, the time during which energy is delivered to the energy delivery device may be increased, or a combination of the two. Alternatively, if the temperature is found to be too high, one or more of the following may occur: the energy delivered by the generator to the energy delivery device may be decreased, the time during which energy is delivered to the energy delivery device may be decreased, or the delivery of energy may be substantially stopped.

In some embodiments, for example if energy is being delivered to a plurality of probes substantially concurrently, the modification of one or more parameters of energy delivery at step 640 may be performed in response to only one of the measurements measured at step 620. For example, the parameter(s) of energy delivery may be modified in response to the maximum temperature measured at step 620, in order to ensure that this maximum temperature doesn't exceed a desired limit.

After assessment of measured parameters at step 630, and modification of at least one energy delivery parameter at step 640, if necessary, an assessment is made at step 650 to continue energy delivery at step 610, or to terminate the procedure. In some embodiments, the assessment of step 650 may be made at any point during the procedure, and may occur more than once during a given time period. This assessment may be based on, for example, user input, total treatment time elapsed, one or more measured or calculated parameters, or on the satisfaction of one or more error conditions inherent to the system. Termination of the procedure need not necessarily entail the cessation of energy delivery and may instead involve switching to a different mode, procedure, or algorithm.

The method of the present invention may also include a step whereby one or more other treatment parameters are modified, for example in response to a measured parameter, such as temperature or impedance, for example. Such treatment parameters may include, but are not limited to: characteristics of the energy delivered (including frequency, voltage, current and power, for example), the number of energy delivery devices operatively coupled and capable of delivering energy, or the configuration of one or more energy delivery devices.

Furthermore, the method of the present invention may additionally comprise other procedures or steps including, but not limited to: insertion of one or more probes into one or more tissues of a body, which may involve, for example, stereotactic insertion, or positioning using pre-prepared guides or stages; supplying stimulation energy to the body to elicit a neural or muscular response; cooling one or more tissues, for example to maintain a lower temperature in the vicinity of an energy delivery device allowing more energy to be applied without undesirably coagulating, searing or burning tissue; applying a pharmaceutical or chemical compound to a site in the body; or performing a surgical procedure such as cutting or removing tissue.

In some particular embodiments, a step of supplying stimulation energy to the body to elicit a neural or muscular response may be performed independently for each energy delivery device coupled to the generator. In other words, since each energy delivery device may be placed at a different location within a patient's body, for example within different tissues of the patient's body, this step is performed independently for each energy delivery device, in order, for example, to assess the proximity of that particular energy delivery device to motor and/or sensory nerves located in the vicinity of that particular energy delivery device. Alternatively, in some procedures, stimulation may be performed using a plurality of energy delivery devices substantially concurrently. For example, in some embodiments, sensory stimulation may be performed independently for each of a plurality of energy delivery devices while motor stimulation may be performed substantially concurrently for the plurality of energy delivery devices.

In some embodiments of a method of the present invention, as described herein above, one or more parameters of energy delivery may be modified in response to one or more measured parameters. In some such embodiments, the parameters of energy delivery are not modified directly by the generator but are rather modified by modifying a separate parameter on which they are dependent.

For example, in embodiments comprising a plurality of energy delivery devices, one or more of the energy delivery devices may have a relatively low measured impedance value when compared to the impedance values associated with the remaining energy delivery devices. This may occur, for example, due to differences in tissue properties into which the energy delivery devices are inserted. In such a scenario, applying an equal voltage across all of the energy delivery devices may result in significantly increased power consumption by the energy delivery device associated with the low impedance value ($P=V^2/R$). Thus, it may be desirable to limit the power delivered by the generator based on the lowest measured impedance value of the measured impedance values associated with each of the energy delivery devices, so as not to exceed the maximum power available to the generator. In some embodiments, the generator is not operable to directly control the power delivered to the energy delivery devices. Rather, other energy delivery parameters, for example voltage and/or current, which determine the power delivered, may be modified in response to the parameter (in this case, impedance) measurement. In one particular example, the maximum voltage applied by the generator may be limited so that the power delivered to the energy delivery devices doesn't exceed the maximum available power.

This feature helps to ensure that, for example, the power delivered to a patient's body does not exceed a pre-specified limit, thus ensuring that the generator itself doesn't fail and also ensuring a safer treatment procedure for the patient.

In some particular embodiments, the dependent parameter, for example the power delivered by the generator, may be measured one or more times throughout the course of a treatment procedure and, if that parameter is approaching a pre-specified limit, then another parameter can be modified. For example, if the power delivered approaches the maximum power available, the generator may then limit the voltage applied to the energy delivery devices, which effectively limits the power delivered by the generator.

Figure 7:
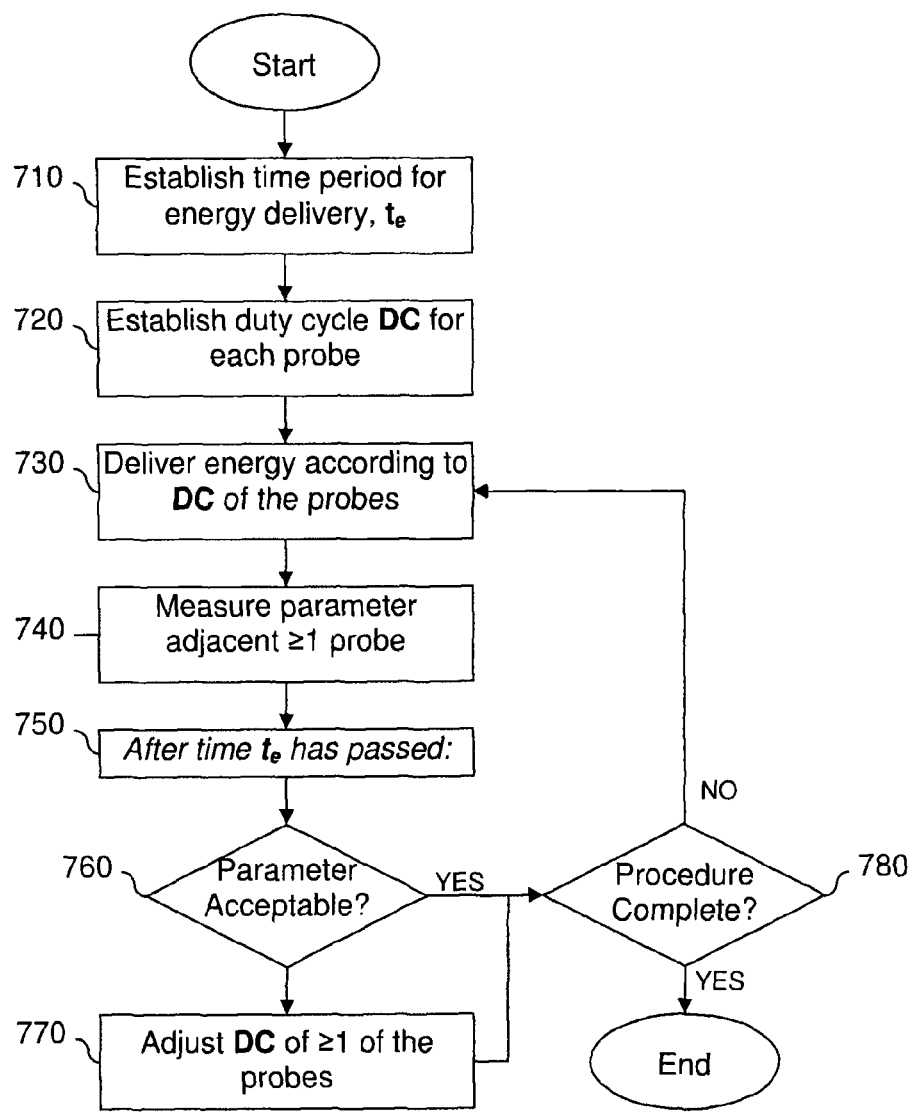
FIGS. 7-10 are flow charts showing various embodiments of methods of delivering energy using a duty cycle.

Having described a general embodiment of a method for delivering energy to a plurality of energy delivery devices, one particular embodiment of such a method will be presently described, with reference to FIG. 7. According to this embodiment, a time period $t_e$ for energy delivery is established at step 710. This time period $t_e$ represents an interval during which each probe may deliver energy according to its duty cycle, whereby the duty cycle comprises a fraction of the time period $t_e$ during which that probe will deliver energy. The delivery of energy to a particular probe during its respective duty cycle is controlled, for example, by controlling a switching means associated with the generator output channel coupled to that probe, in order to substantially allow or substantially prevent the flow of current to that probe, as described herein above.

The time period $t_e$ need not be fixed throughout the course of the treatment procedure and may be adjusted manually or automatically based on any criteria including, but not limited to: the total elapsed treatment time, one or more measured or calculated parameters, or the parameters of the energy being delivered (for example, voltage, current, frequency, or power). In addition, in some embodiments, $t_e$ is related to the controller's integrated cycle time, the period of the repetitive control loop, or some other time representing a feature or design requirement of the system being used or the procedure being performed.

In the context of the present invention, the phrase 'course of treatment procedure' refers to a procedure including one or more iterations of the steps shown in any of FIGS. 7-10, and which may include other procedures or steps that occur before, after, during, or between the steps of FIGS. 7-10. The 'total treatment time elapsed' refers to the total time that has elapsed since the beginning of a 'course of treatment', and may begin at step 710, or may begin at the start of a procedure that precedes step 710, but which is part of the same course of treatment. Other procedures that may be included in a 'course of treatment' may include, but are not limited to: inserting one or more probes into one or more tissues of a body, which may involve, for example, stereotactic insertion, or positioning using pre-prepared guides or stages; supplying stimulation energy to the body to elicit a neural or muscular response; cooling one or more tissues or probes, for example to maintain a lower temperature in the vicinity of a probe allowing more energy to be applied without undesirably coagulating, searing or burning tissue; applying a pharmaceutical or chemical compound to a site in the body; and/or performing a surgical procedure such as surgically cutting or removing tissue.

At step 720, an initial duty cycle from 0-1 is established for each probe, where 1 is equivalent to a length of time equal to time period $t_e$. An initial duty cycle may be determined automatically or manually and may be established based on a number of criteria including, but not limited to, referencing one or more predetermined settings (for example, settings based on the total number of probes, on characteristics of the probe, or on the properties of the tissue into which the probe is inserted), a measured or calculated parameter, or the parameters of the energy being delivered. Not all probes need deliver energy during a given time period $t_e$, and the sum of the duty cycles of the probes may equal 1 (whereby energy is delivered for the entire duration of the time period $t_e$), may be less than 1 (whereby there may be portions of a given time period $t_e$ during which no energy is delivered), or may be greater than 1 (where energy delivery is only partially sequential, and partially concurrent, as described further below).

Figure 11:
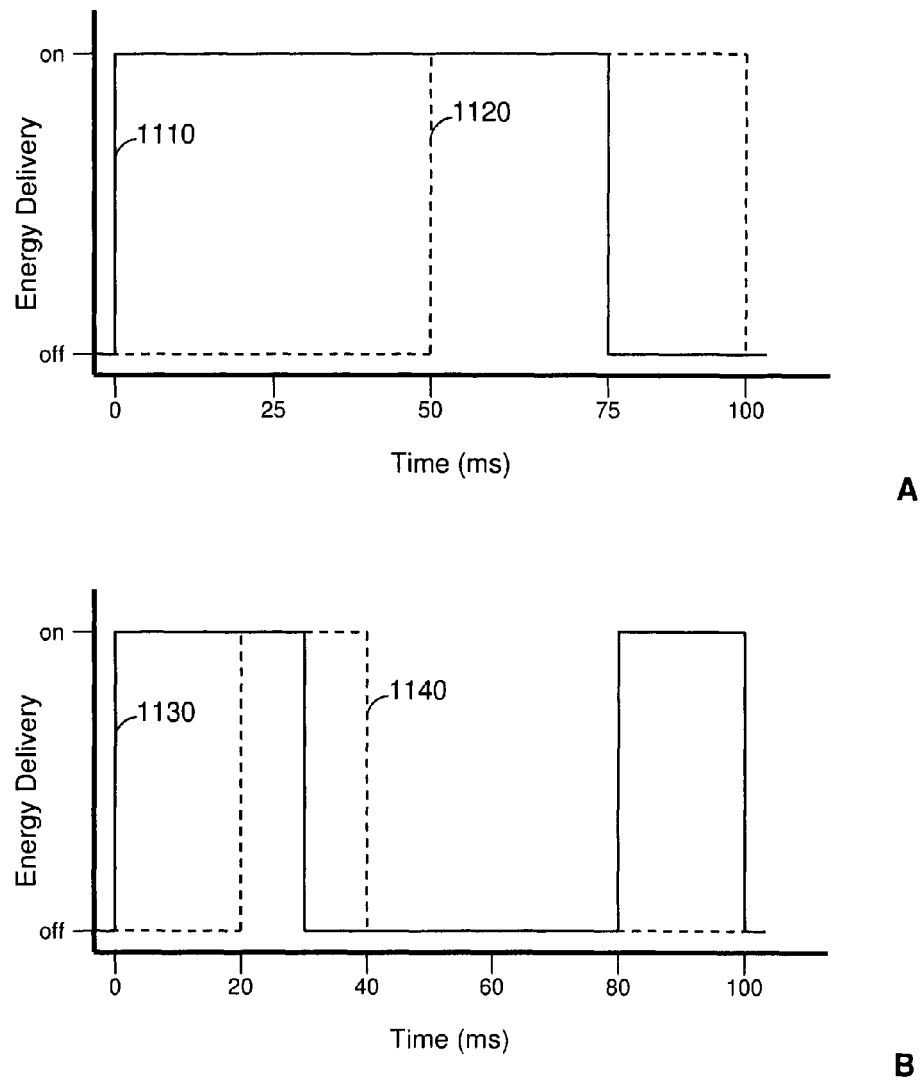
FIGS. 11A and 11B are graphs showing energy delivery vs. time for exemplary duty cycles for a system comprising two probes.

The probes may deliver energy according to their duty cycles in any sequence, and this sequence may be predetermined, may be set by the user, may be based on tissue measurements, or may be randomly or otherwise determined and may change during the course of the treatment procedure. Furthermore, a probe may deliver energy more than once in a given time period $t_e$, as its duty cycle need not correspond to continuous energy delivery, as described herein below, with respect to FIG. 11. The benefit of using a duty cycle is that it allows for individual control of the amount of energy delivered to each probe, which simultaneous delivery with known systems does not allow, but can avoid problems associated with energy dissipation, characteristic of known methods of sequential energy delivery, because regular measurement of tissue parameters and subsequent modification of duty cycles ensures that an appropriate amount of energy is being delivered to each treatment site. In other words, rather than delivering energy substantially sequentially, where each probe is on for a fixed amount of time, employing a variable duty cycle helps to correct for energy dissipation because the duty cycles can vary from one time period $t_e$ to the next time period $t_e$, such that energy delivery in a subsequent time period $t_e$ can be increased to any probe that is deemed to be too 'cold'. In addition, as mentioned hereinabove, time period $t_e$ may be automatically or manually adjusted during the course of a treatment procedure, responsive to one or more factors.

In addition, switching between probes can be accomplished relatively quickly, for example faster than increasing or decreasing the output voltage of the generator. In other words, it may be desirable, in certain situations, to adjust the energy delivered to a particular probe. This may be accomplished, for example, by adjusting the output voltage of the generator or, alternatively, by adjusting the time during which energy is delivered to the probe (as described herein). Adjusting the energy delivered to the probe by adjusting the time during which energy is delivered may be accomplished more quickly relative to increasing or decreasing the output voltage of the generator. This may be useful when the time constant of temperature decay at a treatment site is small, such that a relatively short "off" period (where energy is not being delivered to the probe located at the particular treatment site) is helpful; if the probe were to be "off" too long, then the temperature at that site would drop, compromising the quality of the control system. Thus, in such situations, time control of energy delivery, as described herein, may be particularly desirable.

Following the establishment of the time period $t_e$ and of the initial duty cycles, energy is delivered at step 730 to each treatment site within the patient's body through each probe, according to the respective duty cycles of the probes. If the initial duty cycle of a given probe is 0, that probe will not deliver energy during step 730. As described above, probes may be configured to deliver energy in a variety of configurations, for example, in a monopolar configuration, whereby energy may be delivered via a probe or probes to a separate return electrode, for example, a grounding pad, or in a bipolar configuration, whereby energy flows substantially between two or more probes, or between two or more electrodes on one probe. If two or more probes are used in a bipolar configuration, any probe may be an active or return electrode. In further embodiments, probes may be configured in a multipolar or multiphasic arrangement, whereby the probes are configured such that the electrical potential and/or the phase of energy transmitted to at least two of the probes differs in such a way to cause energy to flow in a desired direction between the probes. In alternate embodiments, other forms of energy may be delivered including microwave energy, ultrasonic energy, thermal energy, or optical energy (for example via a laser).

The energy being delivered to each probe need not have the same parameters. For example, if energy is delivered to two probes sequentially, the voltage, current, frequency or power of energy delivered, for example, may be different for each probe. In addition, the parameters of the energy being delivered may change throughout a course of a treatment procedure and may vary based on one or more of, but not limited to, user input, probe characteristics, one or more measured parameters such as temperature or impedance, or total treatment time elapsed. For example, the power delivered to each probe may be measured during a time period $t_e$ and, in some embodiments, the average power delivered to all of the probes may be calculated. If the power delivered is below an expected level of power delivery, the overall power delivered to the probes may be increased, for example during a subsequent $t_e$.

At step 740, at least one parameter indicative of a property of a tissue to which energy is being delivered is measured. For example, the voltage generated by a thermocouple may be measured, providing a measured parameter indicative of the temperature of the tissue into which the probe is inserted. A wide variety of tissue properties may be measured including, but not limited to: temperature, impedance, density, optical density, thermal conductivity, heat capacity and pH. Different properties may be measured throughout a course of a treatment procedure. The step 740 of measuring may involve the use of any of a variety of measuring devices, and the measuring devices may be integral to or separate from the probes. Multiple measurements may be made with respect to a single tissue property, and multiple tissue properties may be measured. The step 740 of measuring may occur multiple times within a given time period $t_e$ and may occur before, during, and/or after the step 730 of delivering energy.

In one embodiment of the present invention, once an amount of time equal to the time period $t_e$ has passed at step 750, an evaluation is made at step 760 of at least one parameter based on one or more measurements made at step 740 after the delivery of energy at step 730. This evaluation may be based directly on one or more measured parameters, and/or on a parameter derived from a calculation or analysis (including PID analysis) of measured parameters, and may also take into account other treatment parameters, such as total treatment time elapsed, known tissue characteristics, patient history, or parameters of the energy being delivered.

Figure 10:
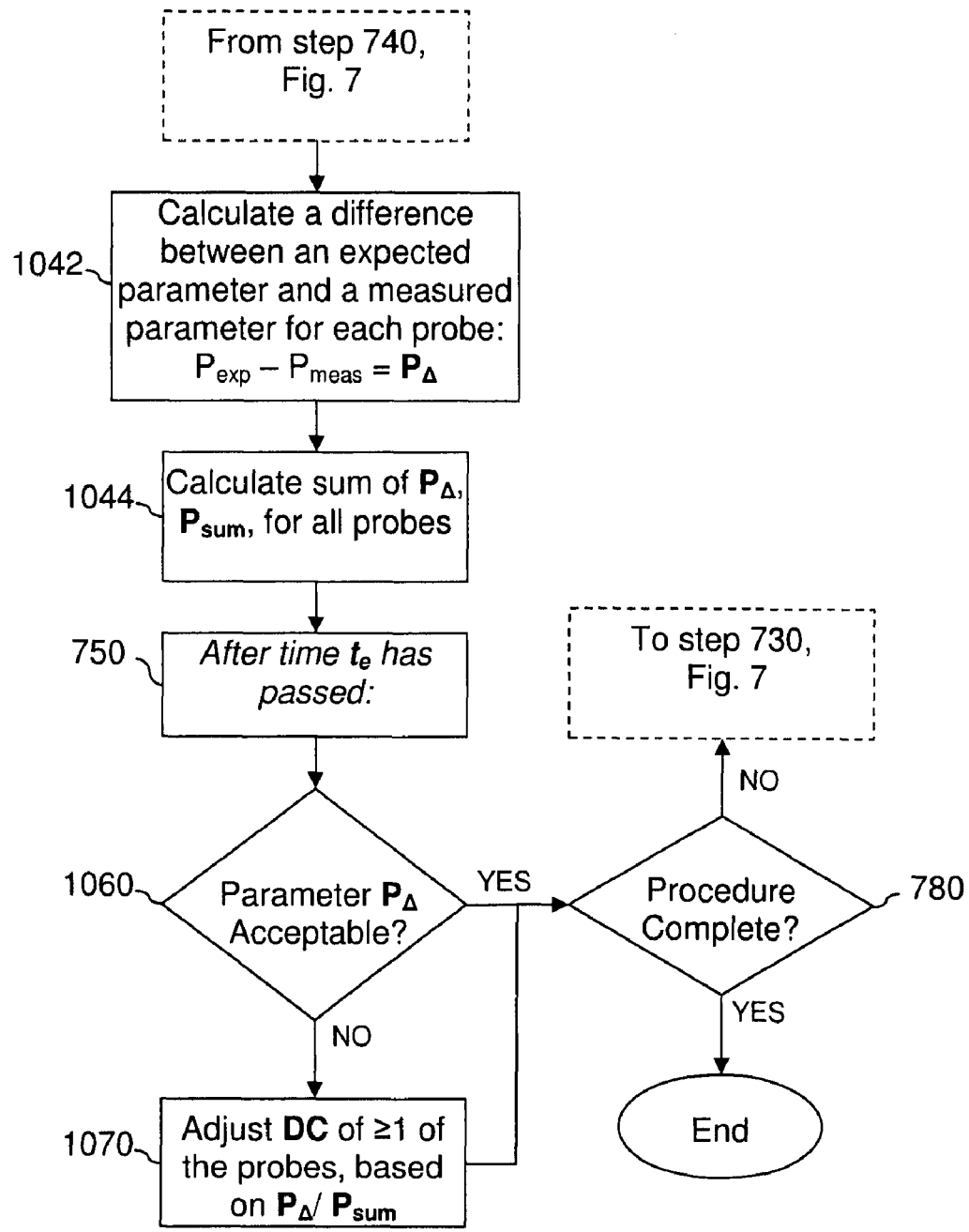

If a parameter, or set of parameters, is found to be unacceptable at step 760, the duty cycle of at least one of the probes will be adjusted at step 770, so that energy will be delivered to that probe for a greater or smaller fraction of the time period $t_e$ the next time energy is delivered at step 730. The adjustment may involve one or more of, but not limited to, increasing or decreasing the duty cycle by a set amount (e.g. adding or subtracting 0.1 from the duty cycle), scaling the duty cycle (e.g. multiplying or dividing the duty cycle by 2), setting the duty cycle to a given value (e.g. setting a duty cycle to 0.25), and/or performing a calculation using one or more parameters to determine the duty cycle (e.g. determining duty cycles based on the relative $P_A$ for more than one probe, as shown in FIG. 10). In some embodiments, $P_A$ is used in a PID control algorithm that is adjusted throughout the course of a treatment procedure that effectively characterizes a given treatment site (at which a particular probe is inserted) to optimally determine the appropriate duty cycle for the probe inserted at that site.

Following the adjustment of duty cycles at step 770, energy is delivered at step 730 according to the new duty cycles, unless the procedure is complete at step 780 (for example, based on the total treatment time elapsed), in which case the procedure is terminated. If all parameters are found acceptable at step 760, energy will be delivered at step 730 using the existing duty cycles, unless the procedure is terminated at step 780. In this way, this embodiment of the method of the present invention can be used to control the total amount of energy delivered by each probe, by controlling the amount of time (as a fraction of $t_e$) that energy is delivered by each probe, i.e. the duty cycle for each probe.

The step 740 of measuring and the step 770 of adjusting (if necessary) may occur at least partially during the step 730 of delivering energy in order that energy delivery be continuous. For example, a determination of how duty cycles will be adjusted (including performing any necessary calculations) may be made during energy delivery at step 730, and once the time period $t_e$ has elapsed at step 750, the new duty cycles will be set and step 730 of the next time period $t_e$ will proceed immediately, without interruption.

In some embodiments, an assessment of whether the procedure is complete at step 780 may be made at any point during the procedure, and may occur more than once during a given time period $t_e$. This assessment may be based on, for example, user input, total treatment time elapsed, one or more measured or calculated parameters, or on the satisfaction of one or more error conditions inherent to the system. As described herein above with respect to FIG. 6, termination of the procedure need not necessarily entail the cessation of energy delivery and may instead involve switching to a different mode, procedure, or algorithm.

Figure 8:
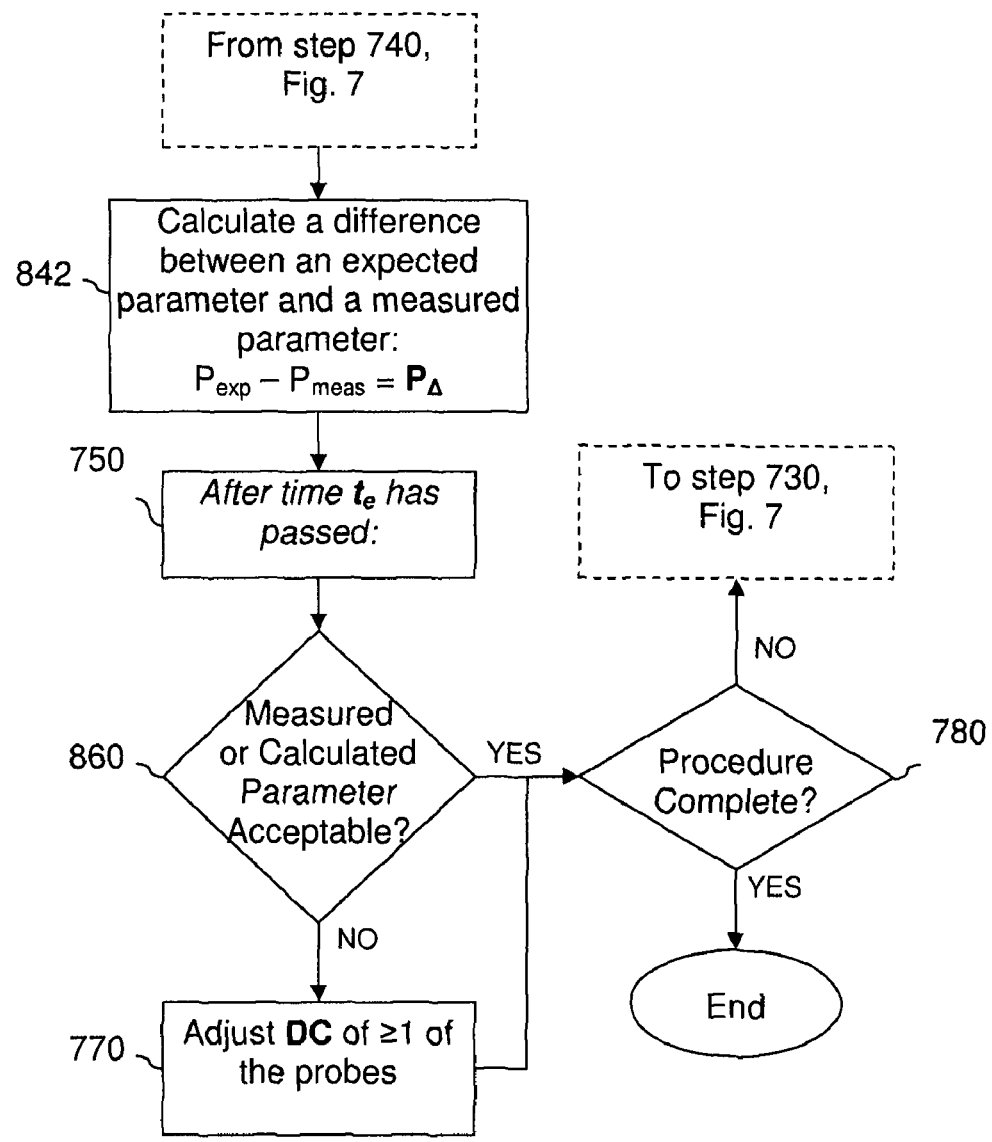
Figure 9:
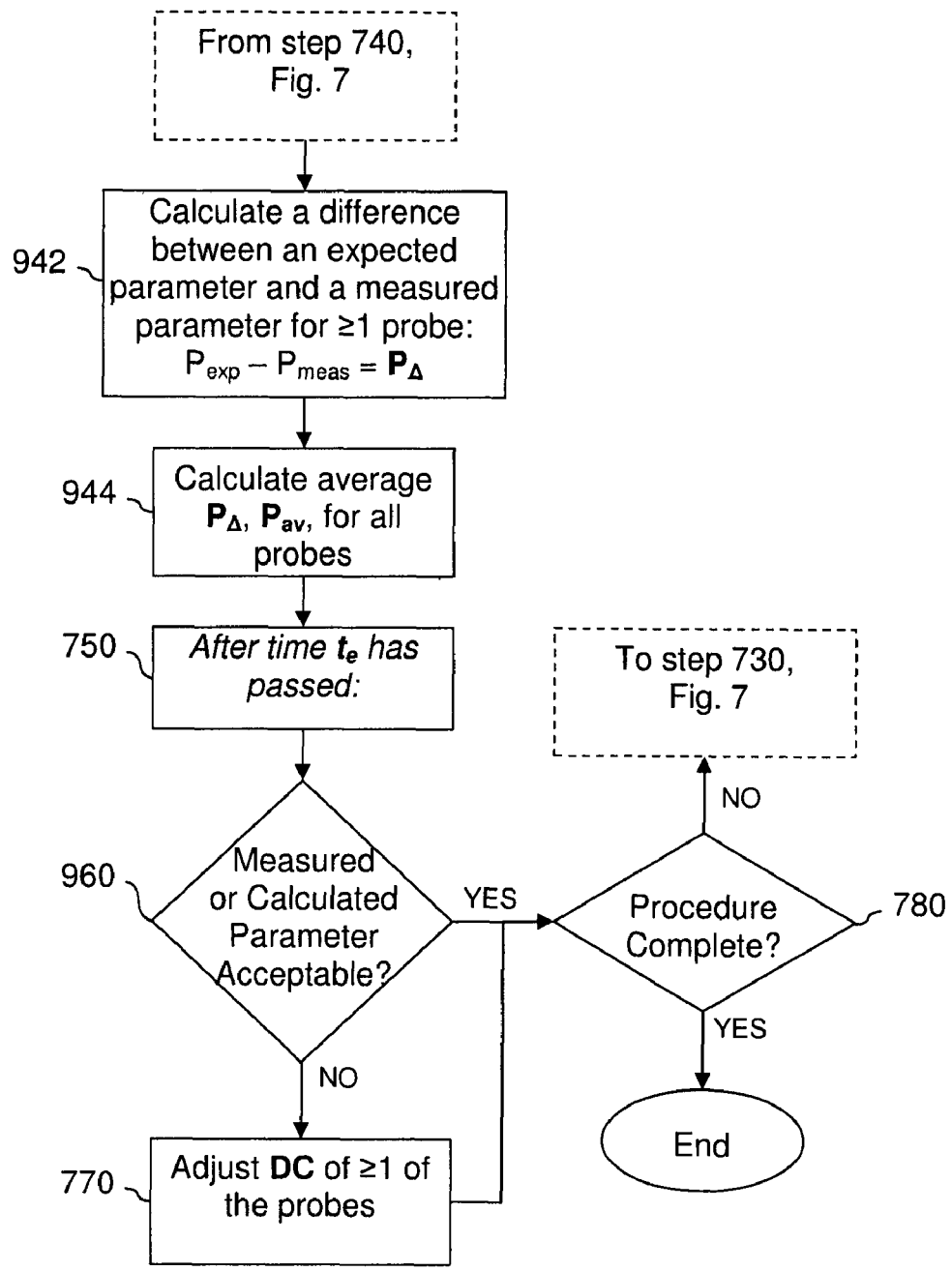

FIGS. 8-10 show various embodiments of the present invention whereby the adjustment of a duty cycle at step 770 is based on one or more calculations made following the step 740 of measuring. In the embodiment shown in FIG. 8, the method of the present invention further comprises a step of calculating a difference, $P_A$, between an expected parameter and at least one measured parameter at step 842 (i.e. $P_A = P_{expected} - P_{measured}$). The value of the expected parameter may be a constant or predetermined value, or may be dependent on one or more treatment variables, including, but not limited to, one or more parameters of the energy being delivered, the total treatment time elapsed, or the value of another measured or calculated parameter. At step 860, the evaluation of at least one parameter may include an evaluation of the difference calculated at step 842.

For example, if the temperature of tissue adjacent a probe is measured to be 50° C., and an expected value is 80° C., then $P_A$ would be 30° C., and the duty cycle of the probe may be increased; whereas, if the measured temperature were 90° C., and the expected value were 80° C., then $P_A$ would be −10° C., and the duty cycle of the probe may be decreased or set to 0. As mentioned herein above, having a plurality of probes allows each probe to be placed in a spaced-apart treatment site, relative to any other probes. In such embodiments, the expected value of a parameter may differ amongst the different treatment sites depending, for example, on the differences in the properties of the tissues at each treatment site. For example, the different treatment sites may comprise different tissues. In some particular embodiments, the tissue at a first treatment site has an initial impedance value different from an initial impedance value of the tissue at a second treatment site. Thus, in accordance with the present invention, the $P_A$ value for each probe is calculated with respect to the specific expected parameter associated with that probe and/or treatment site.

In another embodiment, as shown in FIG. 9, a difference between an expected parameter and a measured parameter is calculated at step 942, as described above, for more than one probe, for example, for each probe, and then an average, $P_{av}$, (for example, a mean) of the differences is calculated at step 944 ($P_{av}=(P_{A1}+P_{A2}+\ldots P_{An}/n)$). At step 960, the evaluation of at least one parameter may include a comparison of a $P_A$ calculated for a probe at step 942, and the $P_{av}$ calculated at step 944.

For example, if temperature measurements taken adjacent 3 probes were 90° C., 65° C. and 40° C. and all probes had an expected temperature of 80° C., then the $P_A$ of each probe would be −10° C., 15° C., and 40° C., respectively, and $P_{av}$ would be 15° C. $P_A$ for each probe could be compared to $P_{av}$ and probes with $P_A > P_{av}$ have their duty cycles increased, probes with $P_A < P_{av}$ could have their duty cycles decreased, and probes with $P_A = P_{av}$ could have their duty cycles remain the same. In this case the 40° C. probe would have its duty cycle increased, the 90° C. probe would have its duty cycle decreased, and the 65° C. probe would have its duty cycle remain the same.

In yet another embodiment, as shown in FIG. 10, following the calculation of a difference, $P_A$, between an expected parameter and a measured parameter, at step 1042, for more than one probe, as described with respect to FIG. 8, the sum of $P_A$ for all probes, $P_{sum}$, is calculated at step 1044. At step 1060, the adjustment of the duty cycle of at least one probe may comprise setting the duty cycle equal to the ratio of: $P_A$ for that probe, and $P_{sum}$. For example, if temperature measurements taken adjacent 3 probes were 70° C., 65° C. and 55° C. and all probes had an expected temperature of 80° C., then the $P_A$ of each probe would be 10° C., 15° C., and 25° C., respectively, and $P_{sum}$ would be 50° C. If the duty cycle for each probe were then set to $P_A/P_{sum}$, then the duty cycles of the 3 probes, respectively would be 0.2, 0.3 and 0.5. In some embodiments, if the $P_A$ for a particular probe is negative (for example if that probe's temperature is above the expected temperature), then that $P_A$ value may be set to 0 with respect to calculating the $P_{sum}$, in which the duty cycle for that particular probe will also be 0 ($P_A/P_{sum}$). In addition, in some embodiments, $P_{sum}$ may be evaluated in order to determine whether or not sufficient energy is being delivered to the probes in order to minimize $|P_{sum}|$. For example, $P_{sum}$ of one $t_e$ may be compared to $P_{sum}$ of a previous $t_e$ in order to determine whether or not the $P_{sum}$ has decreased (where $P_{sum}$ is positive). If not, the overall energy delivered to the probes may be increased. Alternatively, if $P_{sum}$ is negative, the amount of energy delivered may be decreased, in order to allow $P_{sum}$ to approach a value of 0.

In some embodiments, the duty cycle assigned to the hottest probe is transferred to, shifted to or exchanged with the coolest probe, whilst not modifying any other probes whose parameter measurement (e.g. temperature) lies between the two extremes (e.g. hottest and coldest). In this way, the damping of the system can be modified, which may be useful where an underdamped system (oscillatory response) is undesirable. Furthermore, the amount of duty shift that is permitted per time period $t_e$ may be limited, further dampening the system. In some such embodiments, this shifting approach may be modified during a treatment procedure, as may the maximum number of sequential shifts from a given probe (e.g. the hottest probe can only shift for about 10 consecutive time periods $t_e$, at which a different probe is shifted).

In some embodiments of the present invention, the initial value of the power output of the generator may be minimized based on the number of probes connected to the system, the predicted power required, etc. This reduces the requirements for the controller regarding the resolution of the duty cycle. For example, if the generator is delivering 50 W during a given $t_e$, and if a particular probe requires only 0.5 W, then the duty cycle of that probe would be about 0.01, which would therefore require that the controller have a duty cycle resolution of about 1%. However, if the initial power output of the generator is set to 25 W (based on pre-existing knowledge, for example as mentioned above), then the controller would only require a duty cycle resolution of about 2%). Reducing the requirements for the duty cycle resolution may be further beneficial, in that it reduces any potential errors that may be introduced due to specified tolerances of other system components. For example, if the switching controller has a specified tolerance of about 0.1%, then the potential error for a 1% duty cycle would be greater than the potential error for a 2% duty cycle.

In some embodiments of the method of the invention, energy may be delivered only partially sequentially, and at least two probes may deliver energy partially concurrently. In other words, at any given point in time during the course of a treatment procedure, more than one switching means may be 'closed', thus substantially allowing current to flow through more than one output channel of the generator. For example, FIG. 11A is a graph of energy delivery vs. time from an exemplary two probe system with a time period ($t_e$) of 100 ms, where the duty cycle of a first probe is 0.75 and the duty cycle of a second probe is 0.5, as illustrated by lines 1110 and 1120, respectively. In this example, the first probe delivers energy from 0 ms to 75 ms, and the second probe delivers energy from 50 ms to 100 ms, therefore both probes are delivering energy from 50 ms to 75 ms, or for 0.25 of $t_e$.

Duty cycles need not overlap only when their sum is greater than 1 and, in any embodiment, the duty cycle of a probe need not correspond to a period of continuous energy delivery. For example, FIG. 11B shows a graph of energy delivery vs. time for a two probe system with a time period ($t_e$) of 100 ms, where the duty cycle of the first probe is 0.5 (illustrated by line 1130) and the duty cycle of the second probe is 0.2 (illustrated by line 1140), and where the duty cycle of the first probe does not correspond to a period of continuous energy delivery. Any overlap or arrangement of duty cycles is within the scope of the invention, including having the duty cycle of one probe occur substantially concurrently with the duty cycle of another, or, for at least one time period ($t_e$), having at least two probes have at least partially concurrent duty cycles.

During periods where multiple probes are delivering energy at least partially concurrently, the probes may, in some embodiments, deliver energy in a monopolar, bipolar, multipolar, or multiphasic configuration. During periods where multiple probes are delivering energy at least partially concurrently in any configuration, the parameters of the energy being delivered may vary relative to periods where energy is being delivered substantially sequentially. For example, if energy is being delivered through two monopolar probes at least partially concurrently, the energy source may, in some embodiments, deliver twice the power during the time that energy is being delivered concurrently, relative to the time that energy is being delivered sequentially, to compensate for the fact that the power may be split between the two probes during this time.

In one exemplary embodiment of this method aspect of the present invention, the time period ($t_e$) may be in the range of about 10 ms to about 1 s, more particularly about 50 ms to about 100 ms, and the initial duty cycles of the probes may be 1/n, where n is the total number of probes coupled to the generator. In embodiments of a generator comprising a detector 320, as described herein above, the number of probes is automatically detected by the generator, and the initial duty cycles may be automatically set accordingly.

Thus, as described herein above, embodiments of the present invention comprise an energy generator capable of automatically detecting the number of energy delivery devices coupled to the generator. Automatic detection of the number of energy delivery devices coupled to the generator obviates the need for a user to manually indicate the number of energy delivery devices coupled to the generator.

Some such embodiments comprise an energy generator capable of operating in a plurality of functional operating modes, the generator comprising: a mode storage element for storing the operating modes for the generator; a detector for detecting a quantity of energy delivery devices operatively coupled to the generator, the quantity of energy delivery devices being associated with at least one applicable operating mode from the stored operating modes, at least one quantity of energy delivery devices being associated with a plurality of operating modes; a mode selector for selecting a current operating mode from the operating modes applicable to the quantity of energy delivery devices detected where the quantity of energy delivery devices detected is associated with a plurality of operating modes; and an energy controller for controlling a delivery of energy by said generator in accordance with the current operating mode.

This aspect of the present invention allows for fine-tuning of energy delivery algorithms, assigning or expecting certain error conditions (and therefore allowing for greater specificity in the error), increased user convenience, and automatic assignment of settings depending on expected load, amongst other advantages. Current systems cannot accommodate the variability of the application as a function of the number of probes connected to the system.

In addition, embodiments of the present invention provide methods for delivering energy to a body of a human or animal through a plurality of electrosurgical probes, whereby the amount of energy delivered through the probes is controlled, at least in part, by dynamically varying the amount of time that each probe is delivering energy. Employing a variable duty cycle in conjunction with a plurality of probes allows for treatment of spaced apart treatment sites and provides an element of control not found in currently known techniques involving the simultaneous delivery of energy to multiple probes.

Furthermore, in accordance with some particular embodiments of the present invention, a method is disclosed for measuring a parameter and controlling a different parameter indirectly, i.e. through a controllable parameter, in response to the measured parameter.

This aspect of the present invention allows, for example, for rapid adjustments to the maximum applied power, as the tissue impedance can rapidly change or can vary significantly between probes in a procedure involving a plurality of probes. In some embodiments, this aspect of the present invention functions to prevent the electrosurgical system from switching to a low-impedance load after having increased the power, which would result in an "over-power" situation.

In addition, as described herein above, embodiments of the present invention comprise methods for delivering radiofrequency energy in a pulsed manner to a body of a human or animal using a plurality of energy delivery devices. In some particular embodiments, the radiofrequency energy may be delivered to the plurality of energy delivery devices substantially concurrently.

It should be noted that the embodiments of the invention described above are intended to be exemplary only.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An electrosurgical system for performing a procedure on a patient's body, the system comprising:
    a plurality of energy delivery devices, each energy delivery device comprising at least one electrode for delivering electrical energy to a tissue of the patient's body;
    an electrical generator for coupling to the plurality of energy delivery devices such that an output of the generator can be delivered via the plurality of energy delivery devices to produce an effect on the tissue of the patient's body, the generator comprising a detector for detecting a quantity of energy delivery devices coupled to the generator;
    a mode storage element for storing the operating modes of the generator, the quantity of energy delivery devices being associated with at least one applicable operating mode from the stored operating modes;
    a mode selector for selecting a current operating mode from the operating modes applicable to the quantity of energy delivery devices detected; and an energy controller for controlling a delivery of energy by said generator in accordance with the current operating mode.

2. The electrosurgical system of claim 1, wherein at least one quantity of energy delivery devices is associated with a plurality of operating modes and wherein the mode selector is operable to select a current operating mode from the operating modes applicable to the quantity of energy delivery devices detected where the quantity of energy delivery devices detected is associated with a plurality of operating modes.

3. The electrosurgical system of claim 1, wherein the detector is operable to detect the quantity of energy delivery devices coupled to the generator by measuring at least one parameter associated with the energy delivery devices.

4. The electrosurgical system of claim 3, wherein the at least one parameter is selected from the group consisting of temperature and impedance.

5. The electrosurgical system of claim 1, wherein each of the energy delivery devices includes an electrical component having an impedance value and wherein the detector is operable to detect a total effective value of the impedances of the electrical components of all of the energy delivery devices coupled to the generator.

6. The electrosurgical system of claim 5, wherein the electrical component comprises at least one resistor and wherein the total effective value comprises an overall parallel impedance of the resistors of all of the energy delivery devices coupled to the generator.

7. The electrosurgical system of claim 1, further comprising a single cable for coupling the plurality of energy delivery devices to the electrical generator.

8. An electrosurgical method comprising:
coupling a plurality of energy delivery devices to a generator capable of operating in a plurality of functional operating modes;
automatically detecting a quantity of energy delivery devices coupled to the generator;
selecting a current operating mode from the plurality of operating modes of the generator responsive to the detected quantity of energy delivery devices; and
delivering energy in accordance with the current operating mode.

9. A method of performing a procedure on a patient's body, comprising:
coupling a plurality of probes to a generator capable of operating in a plurality of functional operating modes;
automatically detecting a quantity of energy delivery devices coupled to the generator;
selecting a current operating mode from the plurality of operating modes of the generator responsive to the detected quantity of energy delivery devices;
delivering electrical energy in accordance with the current operating mode from the generator to tissue of the patient's body via the plurality of probes to produce an effect on the patient's body;
during the procedure, measuring at least one parameter associated with at least one of the plurality of probes; and
controlling an amount of energy delivered by the at least one of the plurality of probes during the procedure, by varying an amount of time that the at least one of the plurality of the probes is delivering energy responsive to the at least one measured parameter.

10. The method of claim 9, wherein at least one of the plurality of probes is positioned at a first treatment site within the patient's body and wherein at least one other of the plurality of probes is positioned at a second treatment site within the patient's body, the first treatment site and the second treatment site being substantially spaced apart.

11. The method of claim 10, wherein the first treatment site and the second treatment site comprise different tissues.

12. The method of claim 11, wherein the tissue at the first treatment site has an initial impedance value different from an initial impedance value of the tissue at the second treatment site.

* * * * *